Figure 1:
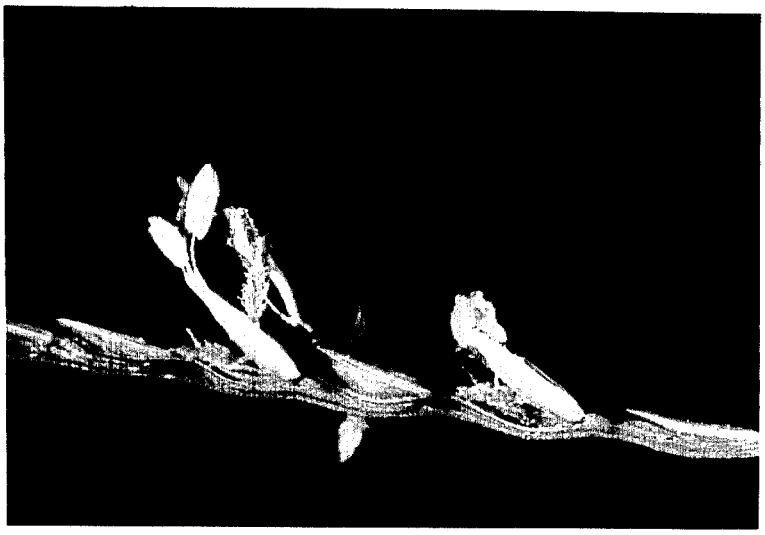

United States Patent [19]

McMaugh et al.

[11] Patent Number: Plant 6,278

[45] Date of Patent: Sep. 6, 1988

[54] *CYNODON DACTYLON* GRASS PLANT — C84-135

[76] Inventors: Peter E. McMaugh, 47 Eastwood Avenue, Eastwood N.S.W. 2122, Australia; Hubert F. Whiting, 28252 Faircrest Way, Escondido, Calif. 92026

[21] Appl. No.: 825,449

[22] Filed: Feb. 3, 1986

[51] Int. Cl.[4] ..... A01H 5/00

[52] U.S. Cl. ..... Plt./88

[58] Field of Search ..... Plt./88

*Primary Examiner*—James R. Feyrer

[57] ABSTRACT

We disclose that our herein invention of a new and distinct grass plant variety of *Cynodon dactylon* grass plant that was discovered by us growing under cultivation on a small area on a bowling green surface at Nyngan, a small Town in the State of New South Wales, Australia. This new claimed grass variety that we have asexually repropagated produces an excellent turfgrass surface retaining green color and growth throughout the winter period in randomized replicated plots compared to the closest known variety of *Cynodon dactylon* grass plant that went dormant losing complete green color and growth. This new claimed grass variety is an attractive dark olive green color, color number 126 D.OLG as defined by the ISCC-NBS centroid color chart and has stigmas of very dark purplish red color, color number 260 V.D.pr as defined by the ISCC-NBS centroid color chart with newly formed anthers before dehiscene of grayish red colork color number 19 GY.RED as defined by the ISCC-NBS centroid color chart. The internode spacings on the stolons are closer together with the stolon being thinner in width. The new claimed variety of grass plant is glabrous except for a few hairs tufted at the sides of the ligule and pubescent on the mature upper leaf surface.

2 Drawing Sheets

The present invention relates to a new and distinct variety of *Cynodon dactylon* grass plant which was discovered by us growing under cultivation on a bowling green located at Nyngan, a small town in the State of New South Wales, Australia, at about 32 degrees south latitude. This new variety of grass plant was observed in the winter time staying green and growing vigorously on a small area of the bowling green surface while all other *Cynodon dactylon* species in the same area was completely dormant and light brown in Color. I broke off several pieces of stolons and rhizomes from the discovered new and distinct variety of *Cynodon dactylon* grass plant I designated C84-135. We broke the stolons and rhizomes into pieces and asexually replanted them into randomized replicated plots to observe and compare the winter color retention and turfgrass qualities against the closest known variety of *Cynodon dactylon* grass plant. Once these plots became established through regular watering and fertilizing, we formed a turfgrass surface through regular mowing. This new and distinct variety C84-135 produced an excellent turfgrass surface when regularly mown. During the following winter we again observed the vigorous growth and green color retention in all replicated plots of this new and distinct variety when compared to the closest known variety of *Cynodon dactylon* grass plant which went completely dormant and brown losing all green color in all relicated plots. During the continued asexual reproduction by us of this new and distinct variety of grass plant C84-135 by stolons and rhizomes, we have confirmed that the above-described characteristics are transmitted through succeeding propagations and have confirmed that the new and distinct variety of grass plant C84-135 has the following unique combination of characteristics. The new and distinct claimed variety is illustrated in the accompanying photographs with the photographs of the closest known variety of *Cynodon dactylon* grass plant. The most noticeable variations between the two grass plants are that the new and distinct claimed variety C84-135 has the following unique combination of characteristics is dark olive green in color and has stigmas of very dark purplish red with newly formed anthers of grayish red. Stolon internode spacings are closer together with the stolon thinner in width. The newly claimed grass variety is glabrous except for a few hairs tufted at the sides of the ligule and pubescent on the mature upper leaf surface.

In the Drawings:

FIG. 1 is a photograph of a spike taken from the same test area, of the new and distinct variety of *Cynodon dactylon* grass plant. This photograph shows the very dark purplish red colored stigmas, color number 260 .v.dpr of the ISCC-NBS centroid color chart of the new and distinct claimed variety of *Cynodon dactylon* grass plant and the grayish red colored anthers, color number 19.gy.red of the ISCC-NBS centroid color chart.

Figure 2:
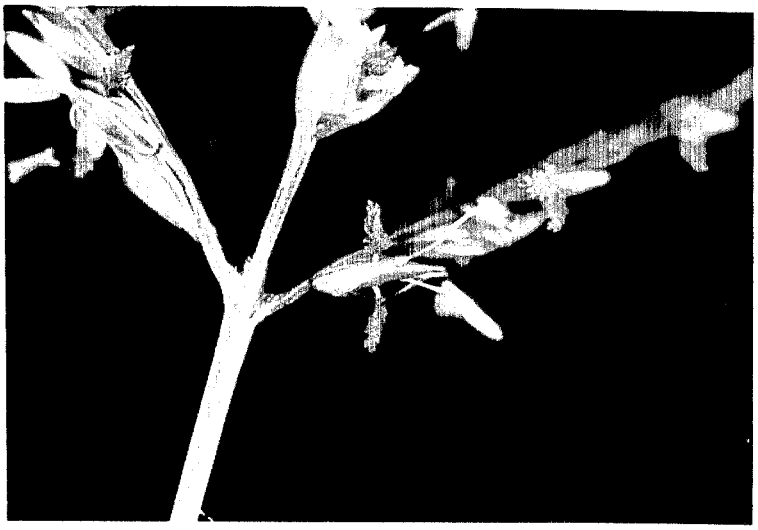

FIG. 2 is a photograph of spikes taken from the same test area, of the closest-known variety of *Cynodon dactylon* grass plant. This photograph shows the very deep purplish red colored stigmas, color number 256 deep pr of the ISCC-NBS centroid color chart and the moderate purplish red colored anthers, color number 258 m.pr of the ISCC-NBS centroid color chart.

Figure 3:
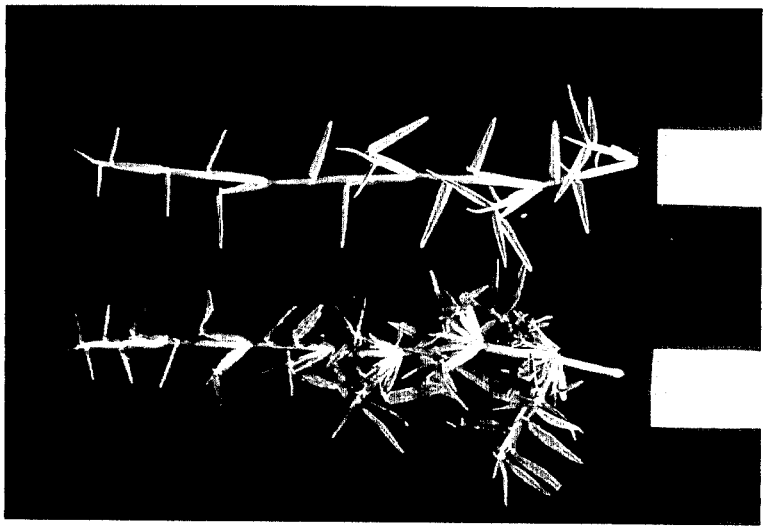

FIG. 3 is a photograph of two pieces of stolons taken from the same test area, the top stolon in the photograph is of the closest-known variety of *Cynodon dactylon* grass plant the bottom stolon in the photograph is the new and distinct variety of *Cynodon dactylon* grass plant. This photograph shows the internodal spaces of the new claimed variety are closer together than the closest known variety and the leaf width of the new claimed variety is wider than the closest known variety of *Cynodon dactylon* grass plant.

Figure 4:
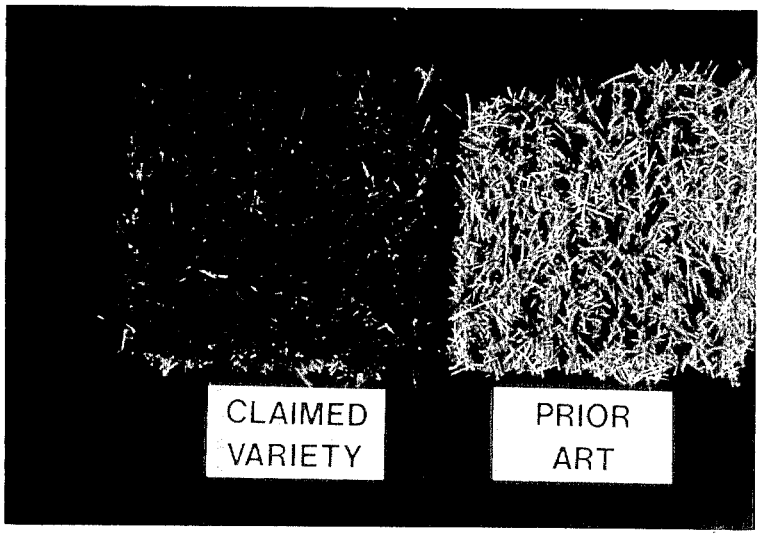

FIG. 4 is a photograph of a top view of sod pieces taken from the same test area of the new and distinct claimed variety of *Cynodon dactylon* grass plant and the closest known variety of *Cynodon dactylon* grass plant (identified by prior art) which sod pieces have been subject to the same mowing conditions at virtually the same time with identical maintenance practices. This photograph shows the dark olive green color, color number 126.d.olg of the ISCC-NBS centroid color chart compared to the closest-known variety of *Cynodon dactylon* grass plant (identified as prior art) which is a moderate green color, color number 145.m.g of the ISCC-NBS centroid color chart.

A detailed description of the new and distinct variety of grass plant is:

(a) An attractive, dark olive green color, number 126 D.OLG of the ISCC-MBS centroid color chart.

(b) The grass is low growing, erect in habit.

(c) The grass spreads by stolons and rhizomes, forming a dense uniform surface with an extensive root system.

(d) Culms vary in height from 10–14 centimeters.

(e) Leaves folded in bud shoot.

(f) The blade is V-shaped in cross-section, keeled and gradually tapering to an acute point.

(g) The first mature leaf is 2–3 millimeters in width and 50–70 millimeters in length.

(h) The grass blade is pubescent on the mature upper leaf surface with a few hairs tufted at the sides of the ligule.

(i) The ligule is a fringe of hairs.

(j) Auricles are absent.

(k) The collar is continuous narrow band.

(l) The sheath is glabrous, split with margins overlapping.

(m) The entire plant is glabrous except for a few hairs tufted at the sides of the ligule and pubescent on the mature upper leaf surface.

(n) The internodal spaces on the stolons are 1.5–2 centimeters and on the culms 2–3 centimeters, the width of the stolon thickness is 1–1.5 millimeters.

(o) The inflorescence consists of 3–4 spikes at the top of the main stem, deflexed at maturity from 30–35 millimeters long.

(p) The spiklets are glabrous in two rows 2–3 millimeters long, blunt at thier base pointed at their tips, borne singly on short branches and glumes are present; the spiklet contains stigmas of very dark purplish red color, color number 260 V.D.PR as defined by the ISCC-NBS centroid color chart with newly formed anthers of grayish red color, color number 19 GY.RED as defined by the ISCC-NBS centroid color chart.

A detailed description of the closest known variety of *Cynodon dactylon* grass plant is:

(a) An attractive moderate green color, color number 145 M.G. of the ISCC-NBS centroid color chart.

(b) The grass is low growing, erect in habit.

(c) The grass spreads by stolons and rhizomes, forming a dense uniform surface with an extensive root system.

(d) Culms vary in height from 8–12 centimeters.

(e) Leaves folded in bud shoot.

(f) The blade is V-shaped in cross-section, keeled and gradually tapering to an acute point.

(g) The first mature leaf is 1.5–2 millimeters in width and 60–80 millimeters in length.

(h) The leaf blade is densely pubescent on the mature upper leaf surface with a few hairs tufted at the sides of the ligule.

(i) The ligule is a fringe of hairs.

(j) Auricles are absent.

(k) The collar is continuous narrow band.

(l) The sheath is glabrous, split with margins overlapping.

(m) The entire plant is glabrous, except for the mature upper leaf surface which is pubescent with a few hairs tufted at the sides of the ligule.

(n) The internodal spaces on the stolons are 3–4 centimeters and on the culms 2–3 centimeters, the width of the stolon thickness is 1.5–2 millimeters.

(o) The inflorescence consists of 3–4 spikes at the top of the main stem deflexed at maturity from 20–35 millimeters long.

(p) The spiklets are glabrous in two rows 2–3 millimeters long, blunt at their base point at their tips, borne singly on short branches and glumes are present; the spiklet contains stigmas of deep purplish red color, color number 256 deep pr of the ISCC-NBS centroid color chart, and anthers of moderate purplish red color, color number 258 M.PR of the ISCC-NBS centroid color chart.

Having now described the new and distinct variety of *Cynodon dactylon* grass plant which we have discovered and asexually reproduced, We claim:

1. A new variety of *Cynodon dactylon* grass plant substantially as described and illustrated a new variety of *Cynodon dactylon* grass plant that was asexually repropagated by us herein shown and described by an olive green color as defined by the ISCC-NBS centroid color chart; this new variety of *Cynodon dactylon* grass plant completely retained growth and green color throughout the winter period and produced an excellent turfgrass surface; the stigmas are of a very dark purplish red color as defined by the ISCC-NBS centroid color chart; the newly formed anthers are of grayish red color as defined by the ISCC-NBS centroid color chart. This new claimed variety of *Cynodon dactylon* grass plant is glabrous except for a few hairs tufted at the sides of the ligule and pubescent on the mature upper leaf surface with stolons thinner in width and the internode spacings closer together.

* * * * *